United States Patent
Mueller

(10) Patent No.: US 8,212,558 B2
(45) Date of Patent: Jul. 3, 2012

(54) MAGNETIC RESONANCE APPARATUS, AND LOCAL COIL AND LOCAL COIL POSITIONING DEVICE THEREFOR

(75) Inventor: Manfred Mueller, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 228 days.

(21) Appl. No.: 12/548,545

(22) Filed: Aug. 27, 2009

(65) Prior Publication Data

US 2010/0052682 A1 Mar. 4, 2010

(30) Foreign Application Priority Data

Aug. 27, 2008 (DE) .................. 10 2008 040 003

(51) Int. Cl.
*G01V 3/00* (2006.01)
(52) U.S. Cl. ........................ 324/307; 324/322
(58) Field of Classification Search .......... 324/300–322; 600/407–445
See application file for complete search history.

(56) References Cited

U.S. PATENT DOCUMENTS

| | | | | |
|---|---|---|---|---|
| 6,045,262 | A * | 4/2000 | Igeta et al. ............. | 378/209 |
| 6,128,522 | A * | 10/2000 | Acker et al. ............ | 600/411 |
| 6,633,658 | B1 * | 10/2003 | Dabney et al. ......... | 382/128 |
| 6,661,227 | B2 | 12/2003 | Eggers et al. | |
| 7,190,164 | B2 * | 3/2007 | Kuhara .................. | 324/309 |
| 7,319,325 | B2 * | 1/2008 | Petot et al. ............. | 324/318 |
| 7,330,030 | B2 * | 2/2008 | Nakabayashi ......... | 324/318 |
| 7,336,076 | B2 * | 2/2008 | Kuhara .................. | 324/318 |
| 8,116,710 | B2 * | 2/2012 | Dent et al. ............. | 455/226.1 |
| 2006/0142655 | A1 | 6/2006 | Petot et al. | |

FOREIGN PATENT DOCUMENTS

| | | |
|---|---|---|
| DE | 195 08 715 A1 | 9/1996 |
| DE | 202008003637 U1 | 6/2008 |

* cited by examiner

*Primary Examiner* — Brij Shrivastav
(74) *Attorney, Agent, or Firm* — Schiff Hardin LLP

(57) ABSTRACT

A magnetic resonance apparatus has a magnet unit at least partially surrounding an examination region, a local coil, and a local coil positioning device. The local coil positioning device includes a transmission device arranged at the local coil to transmit signals and at least one signal reception device arranged at a fixed position relative to the examination region to detect the signals sent by the signal transmission device. A corresponding local coil positioning device comprising a signal transmission device to transmit signals and at least one signal reception device to detect signals sent by the signal transmission device. A local coil for an examination in a magnetic resonance apparatus has a signal transmission device, advantageously an ultrasound signal transmission device. The position of the local coil can be automatically determined by the signal transmission device and the at least one signal reception device without an intervention by a person overseeing the magnetic resonance apparatus being necessary. A positioning of the local coil can thus be conducted particularly quickly and without the risk of an incorrect positioning. The examination duration is reduced, the comfort of the patient is increased and a better utilization of the magnetic resonance apparatus is enabled.

17 Claims, 2 Drawing Sheets

MAGNETIC RESONANCE APPARATUS, AND LOCAL COIL AND LOCAL COIL POSITIONING DEVICE THEREFOR

BACKGROUND OF THE INVENTION

1. Field of the Invention

The invention concerns a magnetic resonance apparatus, a local coil positioning device and a local coil for use in/with the magnetic resonance apparatus.

2. Description of the Prior Art

Magnetic resonance (MR) is a known modality with which images of the inside of an examination subject can be generated. Described simply, the examination subject is positioned in a strong, static, homogeneous basic magnetic field (field strengths from 0.2 Tesla to 7 Tesla and more) in an MR apparatus (scanner) so that his nuclear spins in the subject align along the basic magnetic field. Radio-frequency excitation pulses are radiated into the examination subject to trigger nuclear magnetic resonances. The triggered nuclear magnetic resonances are measured (detected) and MR images are reconstructed based thereon. For spatial coding of the measurement data, rapidly switched magnetic gradient fields are superimposed on the basic magnetic field. The acquired measurement data are digitized and stored as complex numerical values in a k-space matrix. By means of a multidimensional Fourier transformation, an associated MR image can be reconstructed from the k-space matrix populated with such values.

For an improved, spatially precise excitation and measurement of the nuclear magnetic resonances, local coils are used that are positioned directly on the patient to be examined, around an area to be examined (for example knee, head, abdomen etc.). Furthermore, it is sought to optimally position the area (volume) of the patient to be examined (and therefore, if applicable, the local coil) in the center of the examination region of the magnetic resonance apparatus, since the best measurement conditions prevail in that examination region.

For this purpose, it is known to focus on the area of the patient to be examined by means of a light-beam localizer that is located outside of the examination region of the magnetic resonance apparatus at a defined distance from its center, in order to thus determine a travel path that will bring the area to be examined into the center of the examination region. In this technique, a marking line is projected onto a patient bed bearing the patient and the patient bed is moved by an operator of the MR system such that this marking line runs through the area to be examined or the local coil, in order to reference the position of the area to be examined, or the position of the local coil. The travel path can thus be determined. Care must be taken so that the laser beam does not strike an eye of the patient, since otherwise damage to the affected eye can occur. Therefore the patient must possibly close his eyes, and the operator of the MR system has to monitor this. Such a method is described in DE 195 08 715 A1, for example.

SUMMARY OF THE INVENTION

An object of the present invention is to provide a magnetic resonance apparatus, and a local coil positioning device and a local coil therefor, which enable a fast and (for the patient) comfortable positioning of the local coil in the examination region of a magnetic resonance apparatus.

A magnetic resonance apparatus according to the invention has a magnet unit at least partially surrounding an examination region, a local coil; and a local coil positioning device, and the local coil positioning device includes a signal transmission device arranged at the local coil to transmit signals and at least one signal reception device arranged at a fixed position relative to the examination region to detect the signals sent by the signal transmission device.

The position of the local coil can be automatically determined by means of the signal transmission device and the at least one signal reception device without an intervention by a person overseeing or operating the magnetic resonance apparatus being necessary. A positioning of the local coil is thus particularly fast and can be implemented without the risk of an incorrect positioning. Overall the examination duration is reduced, which increases the comfort of the patient and enables a better utilization of the magnetic resonance apparatus.

The signal transmission device is advantageously an ultrasound signal transmission device, and the at least one signal reception device is advantageously an ultrasound signal reception device. The ultrasound signals sent by the signal transmission device and detected by the at least one signal reception device are not perceivable to a patient to be examined and also do not endanger the patient. Patient comfort is therefore increased. In particular, no measures are necessary to avoid risks to the patient that arise from the local coil positioning device (for example the aforementioned closing of the eyes), and therefore they also do not need to be monitored.

A corresponding local coil positioning device has a signal transmission device to transmit signals and at least one signal reception device to detect the signals sent by the signal transmission device. A local coil for an examination in a magnetic resonance apparatus has a signal transmission device for sending signals (different from the MR signals emanating from the coil loop itself) that are suitable for a position determination of the local coil.

The advantages cited with regard to the magnetic resonance apparatus also apply to the local coil positioning device and the local coil.

DESCRIPTION OF THE PREFERRED EMBODIMENTS

Figure 1:
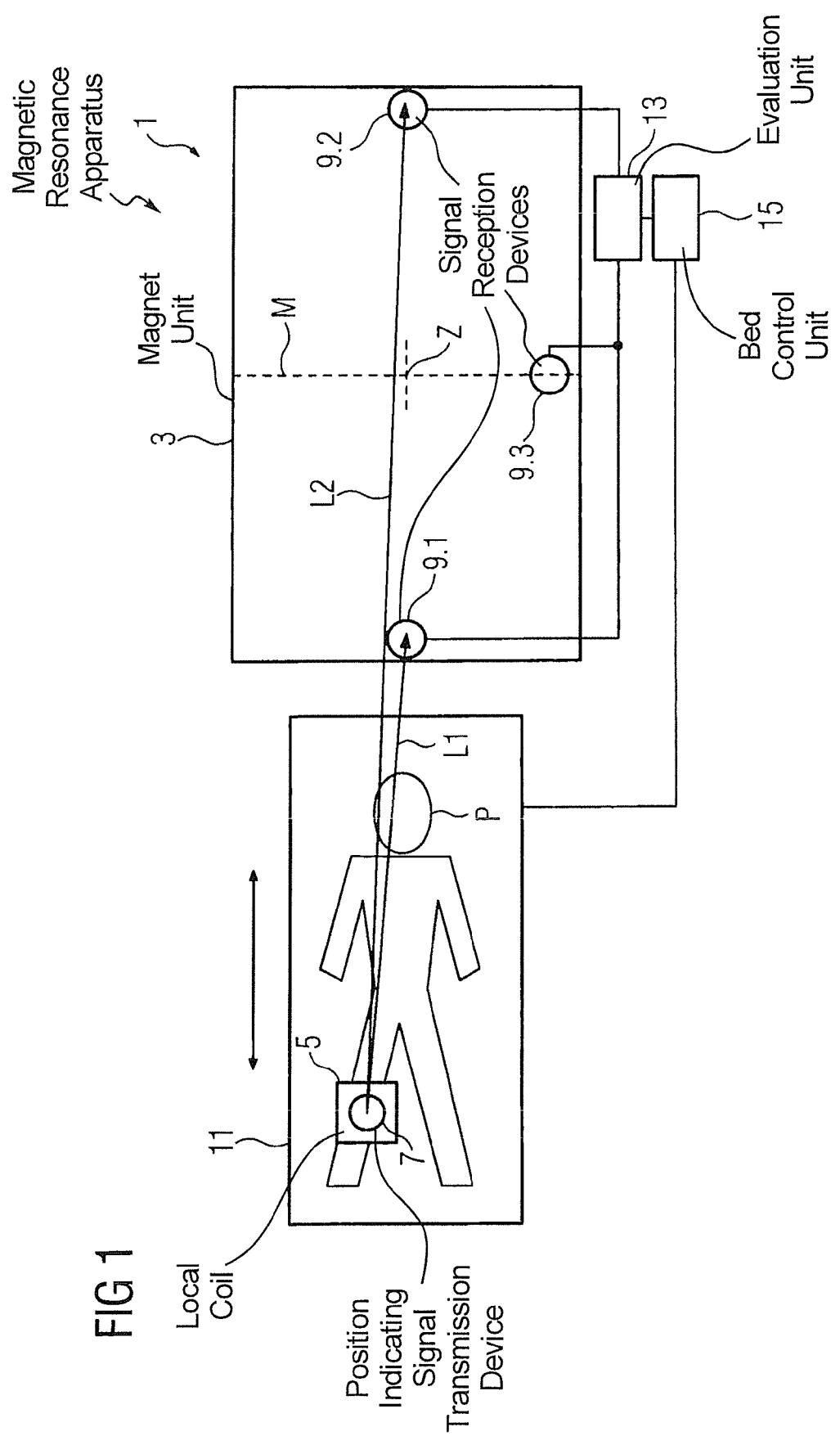
FIG. 1 is a schematic illustration of a magnetic resonance apparatus with a local coil, and a local coil positioning device with the local coil in a first position.
Figure 2:
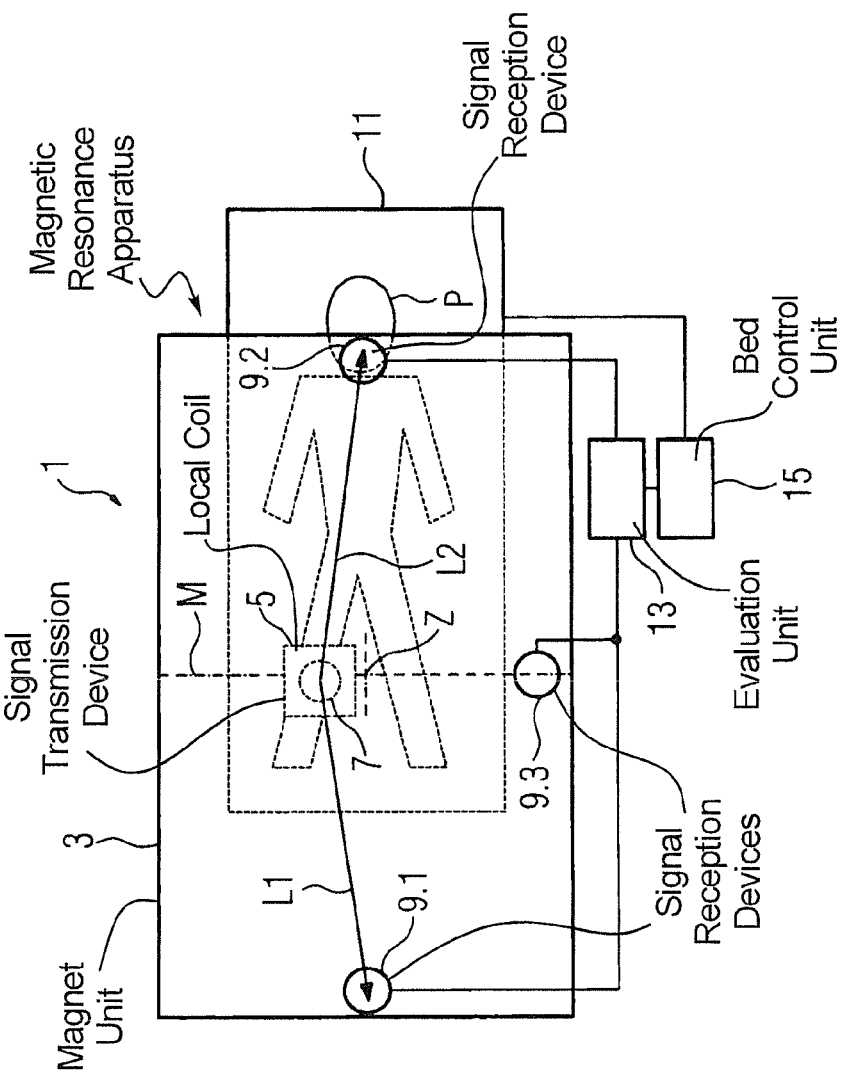
FIG. 2 is a schematic illustration of a magnetic resonance apparatus with a local coil, and a local coil positioning device with the local coil in a second position.

FIGS. 1 and 2 schematically show a drawn magnetic resonance apparatus 1 in a plan view, wherein a local coil 5 of the magnetic resonance apparatus 1 is located at different positions in FIG. 1 and FIG. 2.

The magnetic resonance apparatus 1 is represented by its magnet unit (data acquisition) 3. The basic configuration and operation of a magnetic resonance apparatus are well known, so a detailed description of the individual components and their interactions is not necessary herein.

The magnet unit 3 has a basic field magnet that generates a basic magnetic field and gradient coils that generate gradient fields. The gradient coils are surrounded by a housing. The magnet unit 3 may additionally have a whole body coil (likewise located in the housing) to transmit and receive radio-frequency signals. The magnet unit 3 can be a magnet unit 3 fashioned in the shape of a hollow cylinder, in the hollow space of which is located an examination region in which MR measurements can be conducted, or it may be an open magnet unit with two pole shoes between which the examination region is located. The magnet unit 3 thus at least partially surrounds the examination region.

A patient P can be supported on a patient bed 11 that can be introduced into the examination region. The patient can be brought into the examination region for an examination. A local coil 5 (in the shown example a knee coil) is arranged around an area of the patient P to be examined in order to emit precisely targeted radio-frequency excitation pulses into the area to be examined (here a knee of the patient P) and to receive the resulting magnetic resonance signals. In accordance with the invention, the local coil has a position indicating signal transmission device 7 (i.e., a transmission device that emits signals other than the signals radiated by the radiator of the local coil 5 itself) for the transmission of signals that are suitable for use for a position determination of the local coil. The position-indicating signal transmission device 7 is advantageously an ultrasound transmission device that is preferably integrated into the local coil 5. In each case, the signal transmission device 7 is fashioned such that it can be attached to a local coil.

A situation in which the local coil 5 is located at a position outside of the magnetic resonance apparatus 1 is shown in FIG. 1. For the examination, the area of the patient P to be examined (and therefore the local coil 5 arranged around this area to be examined) should be brought into the center of the examination region. For this purpose, the patient bed 11 is moved into the examination region. Movement of the patient bed 11 is controlled by a bed control unit 15 connected with the patient bed 11. The movement directions are indicated by the double arrow. The bed control unit 15 thereby in particular controls whether, and in which direction, the patient bed 11 is moved, or whether it stands still.

In the shown example, the patient bed 11 must be moved to the right in order to bring the local coil 5 into the center of the examination region. What is meant by the center of the examination region is the plane M running perpendicular to a movement direction (double arrow) of the patient bed 11 through the magnet center Z. For the positioning of the local coil 5, the bed control unit 15 starts the movement of the patient bed 11 in the direction of the examination region; the signal transmission device 7 of the local coil 5 simultaneously emits continuous signals.

To detect the signals sent by the signal transmission device 7, at least one signal reception device 9.1, 9.2, 9.3 is arranged at a fixed position relative to the examination region. The at least one signal reception device is fashioned such that it can be attached to the magnet unit of a magnetic resonance apparatus and/or can be arranged at a fixed position relative to the examination region, for example with corresponding dimensions and suitable mounting devices.

The magnetic resonance apparatus 1 thus has a local coil positioning device that is formed by the signal transmission device 7 and the at least one signal reception device 9.1, 9.2, 9.3. The signal reception devices 9.1, 9.2, 9.3 are thereby advantageously fashioned as ultrasound signal reception devices 9.1, 9.2, 9.3 that detect the signals emitted by the signal transmission device 7 fashioned as an ultrasound signal transmission device. Ultrasound signals are particularly suitable for the position detection of the local coil 5 because they have no disadvantageous interactions with the magnetic and radio-frequency fields occurring in an MR examination, and therefore neither disrupt the examination nor are themselves disrupted by the examination. Moreover, they are also not perceived by the patient P and do not represent any danger to the patient P. Furthermore, the signal transmission device 7 and the at least one signal reception device 9.1, 9.2, 9.3 are MR compatible in the sense described above, i.e. they do not cause harmful interactions with the magnetic and radio-frequency fields that occur in the operation of the MR apparatus.

The local coil positioning device also includes an evaluation unit 13 that is connected with the at least one signal reception device 9.1, 9.2, 9.3, and that is fashioned to evaluate data (in particular the delays L1, L2) of detected signals.

The evaluation unit 13 is advantageously connected with the bed control unit 15 of the magnetic resonance apparatus to transmit the evaluated data thereto. The bed control unit 15 (and therefore the movement of the patient bed 11) thus can therefore be modified or adjusted by means of the evaluated data.

In an advantageous embodiment, two signal reception devices 9.1 and 9.2 are respectively arranged at a start of the magnet unit 3 and at an end of the magnet unit 3 in the travel direction of the patient bed 11. The two signal reception devices 9.1 and 9.2 are thus arranged at a known distance from the center on a straight line through the center of the examination region, wherein the distance is measured along the straight line.

For example, the signal reception devices 9.1 and 9.2 are arranged on the top side of the magnet unit 3, centrally over the entrance into the examination region or, respectively, over the exit from the examination region. The signal reception devices 9.1 and 9.2 are thus equidistant from the center.

During the movement of the patient bed 11, the signal reception devices 9.1 and 9.2 detect the signals emitted by the signal transmission device 7 and relay these to the evaluation unit 13. The evaluation unit 13 evaluates the received signals. In particular the delays L1 and L2 are thereby established.

Different delays L1 and L2 of the respective signals detected by the signal reception devices 9.1 and 9.2 result due to the spatial distance of the signal transmission device 7 from the signal reception devices 9.1 and 9.2.

From the knowledge of the distances of the signal reception devices 9.1 and 9.2 from the center of the magnet of the magnet unit 3, the ratio of the delays L1 and L2 when the signal transmission device 7 (and therefore the local coil 5) is located in the center M can now be determined in a simple manner. For example, given an equidistant arrangement of the signal reception devices 9.1 and 9.2, the local coil 5 is located precisely in the center M of the examination region when the delays L1 and L2 are equal.

If the evaluation of the evaluation unit 13 yields that the ratio of the delays L1 and L2 of the received signals that is calculated from the known ratio of the distances of the signal reception devices 9.1 and 9.2 and indicates the desired position is present, the evaluation unit 13 communicates (via the connection with the bed control unit 15) a control command to the bed control unit 15 that instructs the bed control unit 15 to stop the travel movement of the patient bed 11.

The situation in which the signal reception devices 9.1 and 9.2 are mounted equidistantly far from the magnet center Z (and therefore also from the center M of the examination region), and the local coil 5 is located in the center M of the examination region is shown in FIG. 2. At this point the signals detected by the signal reception devices 9.1 and 9.2 have the same delays L1 and L2. This is established by the evaluation unit 13 as described above, and the bed control unit 15 is instructed to leave the patient bed 11 at this position.

The local coil is thus safely and reliably positioned in the center M of the examination region without an interaction with a person overseeing the examination being necessary.

In an alternative exemplary embodiment, the local coil positioning device is formed by only one signal reception device 9.3 that is itself arranged in the center M of the examination region. For example, the signal reception device 9.3 is mounted on the magnet unit 3.

In this case, the evaluation unit 13 does not compare two detected signals as in the above exemplary embodiment; rather, only the one signal detected by the signal reception device 9.3 is monitored. The evaluation unit 13 establishes how the delays (not shown here) of the detected signals change. As long as the local coil 5 (and therefore the signal transmission device 7) approaches the center M of the examination region, the delays of the signals detected during the movement of the patient bed 11 (which delays are evaluated by the evaluation unit 13) decrease. As soon as the local coil 5 is moved beyond the center M of the examination region, the evaluated delays increase again. If the evaluation unit 13 establishes that the delays are increasing again, it sends a signal to the bed control unit 15 that prompts the bed control unit 15 to reverse the travel direction of the patient bed 11. However, it is may be sufficient (for example given a sufficiently high evaluation rate) for the evaluation unit 13 at this point to already send a signal to the bed control unit 15 that prompts the bed control unit 15 to hold the patient bed 11 at this position.

If the evaluation unit 13 initiates a reversal of the travel direction of the patient bed 11, it is advantageous for the evaluation unit 13 to always store the value of the smallest evaluated delay, and to instruct the bed control unit 15 to stop the movement of the patient bed 11 precisely when this value occurs again after the reversal.

The local coil 5 can also be quickly and safely brought into the center Z of the examination region in this way.

Although modifications and changes may be suggested by those skilled in the art, it is the intention of the inventor to embody within the patent warranted hereon all changes and modifications as reasonably and properly come within the scope of his contribution to the art.

I claim as my invention:

1. A magnetic resonance apparatus comprising:
   a magnetic resonance data acquisition unit that at least partially surrounds an examination region;
   a magnetic resonance local coil configured to radiate radio-frequency signals and to receive resulting magnetic resonance signals; and
   a local coil positioning device comprising a signal transmitter at said local coil that emits wireless, humanly imperceptible position-indicating signals that are different from, and do not interfere with, said RF signals, and at least one signal receiver located at a fixed position relative to said examination region, that wirelessly detects said position-indicating signals emitted by said signal transmitter.

2. A magnetic resonance apparatus as claimed in claim 1 wherein said at least one signal receiver is located at said magnetic resonance data acquisition device.

3. A magnetic resonance apparatus as claimed in claim 1 wherein said local coil positioning device further comprises an evaluation unit in communication with said at least one signal receiver, said evaluation unit being configured to evaluate said position indicating signal to identify a position of said local coil in said magnetic resonance data acquisition device.

4. A magnetic resonance apparatus as claimed in claim 3 comprising a movable patient bed, configured to receive an examination subject thereon, and a bed control unit that controls movement of said patient bed relative to said examination region, said control unit being in communication with said evaluation unit and controlling said movement of said patient bed dependent on the evaluation of the position indicating signal by said evaluation unit.

5. A magnetic resonance apparatus as claimed in claim 1 wherein said local coil positioning device comprises two signal receivers each located at a known distance from a center of the examination region on a straight line proceeding through said center of the examination region.

6. A magnetic resonance apparatus as claimed in claim 5 wherein said signal receivers are respectively located equidistantly from said center.

7. A magnetic resonance apparatus as claimed in claim 1 wherein said signal transmitter is an ultrasound signal transmitter and wherein said at least one signal receiver is an ultrasound signal receiver.

8. A magnetic resonance apparatus as claimed in claim 1 wherein said local positioning device is comprised of magnetic resonance-compatible materials.

9. A local coil positioning device comprising:
   a signal transmitter configured to be affixed to a magnetic resonance local coil that emits wireless, humanly imperceptible position-indicating signals that are different from, and do not interfere with, RF signals emitted by the local coil; and
   at least one signal receiver configured to be located at a fixed position that wirelessly detects said position-indicating signals emitted by said signal transmitter.

10. A local coil positioning device as claimed in claim 9 wherein said at least one signal receiver is located at a magnetic resonance data acquisition device.

11. A local coil positioning device as claimed in claim 10 wherein said local coil positioning device further comprises an evaluation unit in communication with said at least one signal receiver, said evaluation unit being configured to evaluate said position indicating signal to identify a position of said local coil in said magnetic resonance data acquisition device.

12. A local coil positioning device as claimed in claim 10 wherein said local coil positioning device comprises two signal receivers each located at a known distance from a center of an examination region of the magnetic resonance data acquisition device on a straight line proceeding through said center of the examination region.

13. A local coil positioning device as claimed in claim 12 wherein said signal receivers are respectively located equidistantly from said center.

14. A local coil positioning device as claimed in claim 9 wherein said signal transmitter is an ultrasound signal transmitter and wherein said at least one signal receiver is an ultrasound signal receiver.

15. A local coil positioning device as claimed in claim 9 wherein said local coil positioning device is comprised of magnetic resonance-compatible materials.

16. A magnetic resonance local coil comprising:
   a coil radiator configured to radiate radio-frequency signals into an examination subject to excite magnetic resonances in the examination subject, and to detect magnetic resonance signals produced by said magnetic resonances; and
   a signal transmitter configured to emit wireless, humanly imperceptible position indicating signals in a form allowing identification of a position of the local coil therefrom, said position-indicating signals being different from, and do not interfere with, said radio-frequency signals.

17. A local coil as claimed in claim 16 wherein said signal transmitter is an ultrasound signal transmitter.

* * * * *